(12) United States Patent
Hafer et al.

(10) Patent No.: US 10,265,431 B2
(45) Date of Patent: Apr. 23, 2019

(54) VOLATILE DIFFUSER PODS AND RELATED SYSTEMS

(71) Applicant: Henkel IP & Holding GmbH, Duesseldorf (DE)

(72) Inventors: Kevin Hafer, Scottsdale, AZ (US); Alex Hamilton, Phoenix, AZ (US)

(73) Assignee: Henkel IP & Holding GmbH (DE)

( * ) Notice: Subject to any disclaimer, the term of this patent is extended or adjusted under 35 U.S.C. 154(b) by 126 days.

(21) Appl. No.: 15/617,776

(22) Filed: Jun. 8, 2017

(65) Prior Publication Data

US 2018/0353636 A1    Dec. 13, 2018

(51) Int. Cl.
| | | |
|---|---|---|
| *A61L 9/12* | (2006.01) | |
| *A61L 9/03* | (2006.01) | |
| *B01F 3/04* | (2006.01) | |
| *B05B 7/00* | (2006.01) | |

(52) U.S. Cl.
CPC .... *A61L 9/12* (2013.01); *A61L 9/03* (2013.01); *A61L 9/122* (2013.01); *B01F 3/04007* (2013.01); *B05B 7/0081* (2013.01); *A61L 2209/133* (2013.01)

(58) Field of Classification Search
CPC .... A61L 9/03; A61L 9/12; A61L 9/122; B01F 3/04; B01F 3/04007
USPC .............. 261/30, DIG. 88; 422/124
See application file for complete search history.

(56) References Cited

U.S. PATENT DOCUMENTS

| | | |
|---|---|---|
| 2,103,609 A | 12/1937 | Bradburn |
| 2,642,310 A | 6/1953 | Meek et al. |
| 3,990,848 A | 11/1976 | Corris |
| 3,993,444 A | 11/1976 | Brown |
| 4,035,451 A | 7/1977 | Tringali |
| 4,065,261 A | 12/1977 | Fukada |
| 4,111,655 A | 9/1978 | Quincey |
| 4,173,604 A | 11/1979 | Dimacopoulos |
| 4,271,092 A | 6/1981 | Sullivan et al. |
| 4,294,778 A | 10/1981 | DeLuca |
| 4,301,095 A | 11/1981 | Mettler et al. |
| 4,383,951 A | 5/1983 | Palson |

(Continued)

FOREIGN PATENT DOCUMENTS

| | | | | |
|---|---|---|---|---|
| CN | 202288956 U | * | 7/2012 | ............... A61L 9/03 |
| CN | 203060373 U | * | 7/2013 | ............... A61L 9/03 |

(Continued)

*Primary Examiner* — Robert A Hopkins
(74) *Attorney, Agent, or Firm* — Bojuan Deng

(57) ABSTRACT

A system for diffusing one or more volatile compounds carried by a volatile compound mass is provided, including a base carrying a selectively activatable airflow generator and having a base outlet port defined therein. A resealable pod can include a tray and a cover, moveable relative to one another, and collectively defining a containment chamber that contains the volatile compound mass. The containment chamber has an inlet and an outlet, being openable and closeable by relative movement of the tray and the cover. The pod is positionable upon the base such that the base outlet port is in fluid communication with the chamber inlet to enable airflow generated by the airflow generator to pass through the base outlet port, the chamber inlet, the containment chamber, and the chamber outlet to thereby diffuse the one or more volatile compounds carried by the volatile compound mass.

20 Claims, 4 Drawing Sheets

(56) References Cited

U.S. PATENT DOCUMENTS

| | | |
|---|---|---|
| 4,432,938 A | 2/1984 | Meetze, Jr. |
| 5,012,961 A | 5/1991 | Madsen et al. |
| 5,050,798 A | 9/1991 | Sullivan |
| 5,126,078 A | 6/1992 | Steiner et al. |
| 5,234,162 A | 8/1993 | Sullivan |
| 5,335,446 A | 8/1994 | Shigetoyo |
| 5,498,397 A | 3/1996 | Horng |
| 5,547,616 A | 8/1996 | Dancs et al. |
| 5,662,835 A | 9/1997 | Collingwood |
| 5,820,792 A | 10/1998 | Lin |
| 5,932,147 A | 8/1999 | Chen |
| 6,050,551 A | 4/2000 | Anderson |
| 6,080,367 A | 6/2000 | Lin |
| 6,371,450 B1 | 4/2002 | Davis et al. |
| 6,555,068 B2 | 4/2003 | Smith |
| 6,592,104 B2 | 7/2003 | Cox |
| 6,631,888 B1 | 10/2003 | Prueter |
| 6,938,883 B2 | 9/2005 | Adams et al. |
| 7,040,549 B2 | 5/2006 | Rodgers |
| 7,175,815 B2 | 2/2007 | Yamasaki et al. |
| 7,204,870 B2 | 4/2007 | Zobele et al. |
| 7,244,398 B2 | 7/2007 | Kotary et al. |
| 7,382,975 B2 | 6/2008 | Caserta et al. |
| 7,499,632 B2 | 3/2009 | Granger et al. |
| 7,527,247 B1 | 5/2009 | Krueger |
| 7,597,308 B1 | 10/2009 | Stucki |
| 7,621,511 B2 | 11/2009 | Hayes-Pankhurst et al. |
| 7,648,127 B2 | 1/2010 | Cittadino |
| 7,833,492 B2 | 11/2010 | Schumacher et al. |
| 7,917,018 B2 | 3/2011 | Schumacher et al. |
| 7,931,213 B2 | 4/2011 | Ousley |
| 7,959,132 B2 | 6/2011 | Butler et al. |
| 8,133,440 B2 | 3/2012 | Jorgensen |
| 8,137,629 B2 | 3/2012 | Faber et al. |
| 8,367,011 B2 | 2/2013 | Yamamoto |
| 8,385,730 B2 | 2/2013 | Bushman et al. |
| 8,517,351 B2 | 8/2013 | Sharma |
| 8,524,158 B2 | 9/2013 | Shi et al. |
| 8,551,409 B2 | 10/2013 | Yamamoto et al. |
| 8,603,397 B2 | 12/2013 | Gruenbacher et al. |
| 8,673,223 B1 | 3/2014 | Finlay |
| 8,807,538 B2 | 8/2014 | Sharma |
| 8,807,539 B2 | 8/2014 | Hou |
| 8,807,540 B2 | 8/2014 | Sharma et al. |
| 8,876,086 B2 | 11/2014 | Burke et al. |
| 8,925,905 B2 | 1/2015 | Vieira |
| 9,149,031 B2 | 10/2015 | Shi et al. |
| 9,155,813 B2 | 10/2015 | Westphal et al. |
| 9,265,853 B2 | 2/2016 | Scott et al. |
| 9,352,062 B2 | 5/2016 | Klemm et al. |
| 9,352,064 B2 | 5/2016 | Furner et al. |
| 9,393,337 B2 | 7/2016 | Gruenbacher et al. |
| 9,585,982 B1 | 3/2017 | Hafer et al. |
| 2003/0175148 A1 | 9/2003 | Kvietok et al. |
| 2006/0043619 A1 | 3/2006 | Brown et al. |
| 2006/0081721 A1 | 4/2006 | Caserta et al. |
| 2007/0158456 A1 | 7/2007 | Spector |
| 2009/0212124 A1 | 8/2009 | Kenny |
| 2011/0027124 A1 | 2/2011 | Albee et al. |
| 2012/0000989 A1 | 1/2012 | Bordier |
| 2012/0181350 A1 | 7/2012 | Snider |
| 2013/0328223 A1 | 12/2013 | Sharma et al. |
| 2015/0297774 A1 | 10/2015 | Thompson et al. |

FOREIGN PATENT DOCUMENTS

| | | |
|---|---|---|
| WO | WO 2015/092103 A1 | 6/2015 |
| WO | WO 2015/161266 A1 | 10/2015 |

* cited by examiner

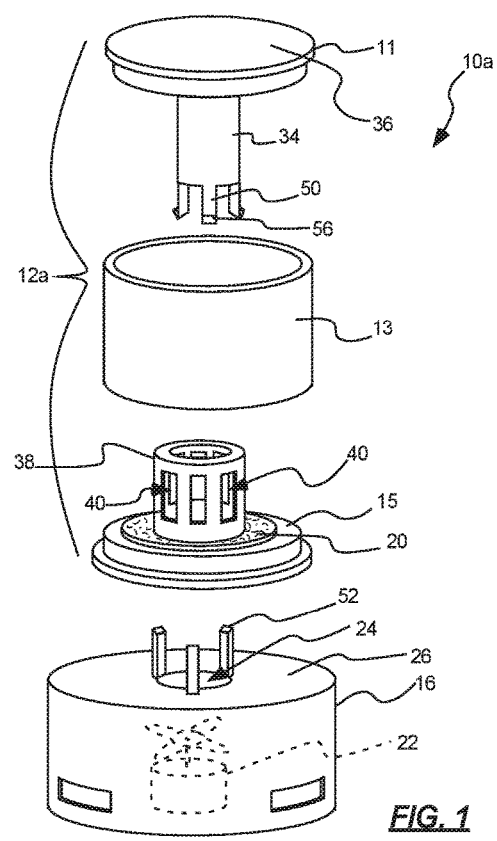
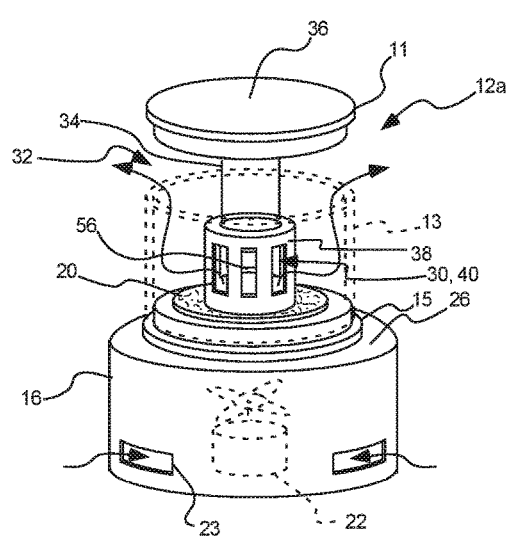

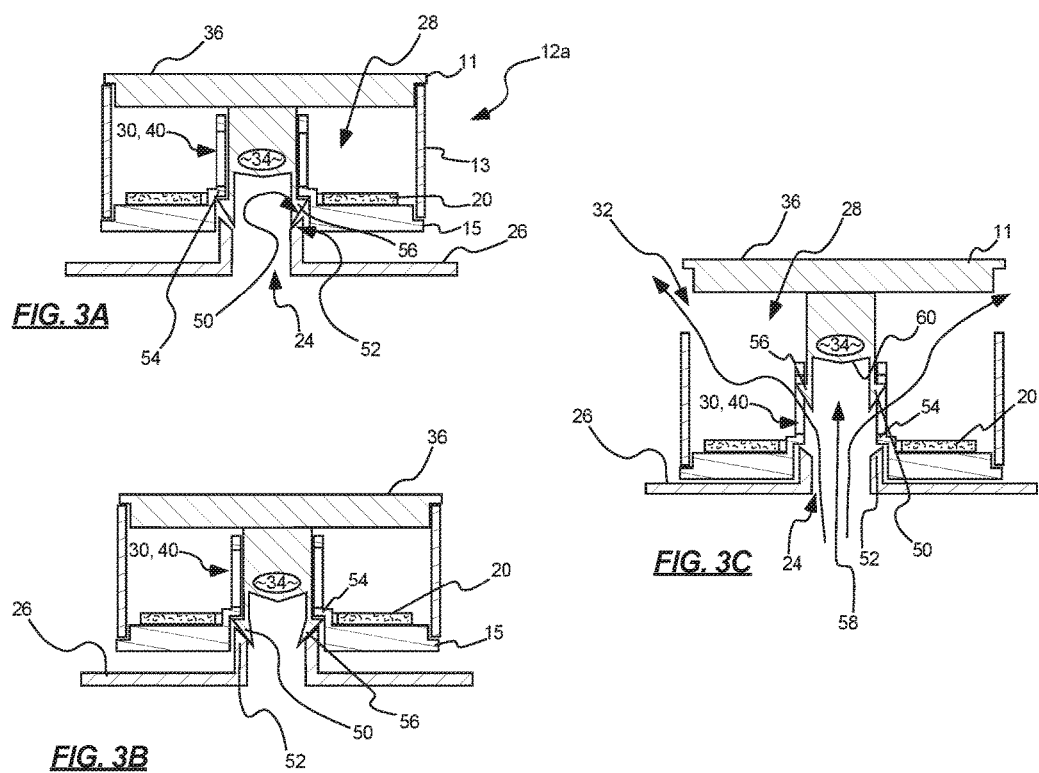

VOLATILE DIFFUSER PODS AND RELATED SYSTEMS

BACKGROUND OF THE INVENTION

Field of the Invention

The present invention relates generally to systems for diffusing volatile compounds such as fragrant materials, disinfectants and pesticides.

Related Art

There exist a variety of systems that diffuse volatile compounds into an environment. One such example is the well-known air freshener that diffuses scented materials to freshen the air of homes, vehicles, offices and the like. Air fresheners such as these can be as simple as cardstock impregnated with a volatile compound, or as sophisticated as electronic systems that selectively diffuse measured quantities of liquefied compounds at varying frequency and potency.

While many such systems exist, consumers continue to seek reliable, easy-to-use products that provide rapid fragrance ramp-up times and that provide flexibility to the consumer in choice of fragrance type.

SUMMARY OF THE INVENTION

In accordance with one aspect of the invention, a system for diffusing one or more volatile compounds carried by a volatile compound mass is provided. The system can include a base carrying a selectively activatable airflow generator and having a base outlet port defined therein. A resealable pod can include a tray and a cover, moveable relative to one another. The tray and the cover can collectively define a containment chamber that contains the volatile compound mass, the containment chamber having an inlet and an outlet, the chamber inlet and outlet being openable and closeable by relative movement of the tray and the cover. The pod can be positionable upon the base such that the base outlet port is in fluid communication with the chamber inlet to enable airflow generated by the airflow generator to pass through the base outlet port, through the chamber inlet, through the containment chamber, and through the chamber outlet to thereby diffuse the one or more volatile compounds carried by the volatile compound mass.

In accordance with another aspect of the invention, a system for diffusing one or more volatile compounds carried by a volatile compound mass is provided. The system can include a resealable pod that includes a tray and a cover, moveable relative to one another. The tray and the cover can collectively define a containment chamber that contains the volatile compound mass. The containment chamber can have an inlet and an outlet, the chamber inlet and outlet being openable and closeable by relative movement of the tray and the cover. The pod can be positionable upon a base having an outlet port formed therein such that the base outlet port is in fluid communication with the chamber inlet to enable airflow generated by an airflow generator carried by the base to pass through the base outlet port, through the chamber inlet, through the containment chamber, and through the chamber outlet to thereby diffuse the one or more volatile compounds carried by the volatile compound mass.

In accordance with another aspect of the invention, a system for diffusing one or more volatile compounds carried by a volatile compound mass is provided, including a base carrying a selectively activatable airflow generator and having a base outlet port defined therein. A resealable pod can include a tray and a cover, moveable relative to one another, the tray and the cover collectively defining a containment chamber that contains the volatile compound mass. The containment chamber can have an inlet and an outlet, the chamber inlet and outlet being openable and closeable by relative movement of the tray and the cover. A pod inlet channel can be in fluid communication with the chamber inlet. A deflector panel can be positioned upstream of the chamber inlet, the deflector panel operable to change a direction of airflow traveling through the pod inlet channel. The pod can be positionable upon the base such that the base outlet port is in fluid communication with the pod inlet channel to enable airflow generated by the airflow generator to pass through the base outlet port, through the pod inlet channel, through the chamber inlet, through the containment chamber, and through the chamber outlet to thereby diffuse the one or more volatile compounds carried by the volatile compound mass.

In accordance with another aspect of the invention, a system for diffusing one or more volatile compounds carried by a volatile compound mass is provided, including a base carrying a selectively activatable airflow generator and having a base outlet port defined therein. Pod engagement structure can be coupled to the base. A resealable pod can include a tray and a cover, moveable relative to one another, the tray and the cover collectively defining a containment chamber that contains the volatile compound mass, the containment chamber having an inlet and an outlet, the chamber inlet and outlet being openable and closeable by relative movement of the tray and the cover. Base engagement structure can be coupled to the pod, the base engagement structure operable to move the tray and cover relative to one another when the pod engagement structure is engaged by the base engagement structure. The pod can be positionable upon the base such that when the base outlet port is placed in fluid communication with the chamber inlet, the base engagement structure engages the pod engagement structure to move the tray and cover relative to one another to cause the chamber inlet and outlet to open.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 1 is a perspective, exploded view of a system for diffusing volatile compounds in accordance with an embodiment of the invention;

FIG. 2 is a perspective view of the system of FIG. 1, shown assembled and open for use;

FIG. 3A is a side, partially sectioned and simplified view of the system of FIG. 1, shown immediately prior to a pod being installed upon a base, with the pod shown in a closed or sealed configuration;

FIG. 3B is a side, partially sectioned and simplified view of the system of FIG. 1, shown with the pod partially installed upon the base;

FIG. 3C is a side, partially sectioned and simplified view of the system of FIG. 1, shown with the pod fully installed upon the base and the pod open for use;

DETAILED DESCRIPTION

Figure 4A:
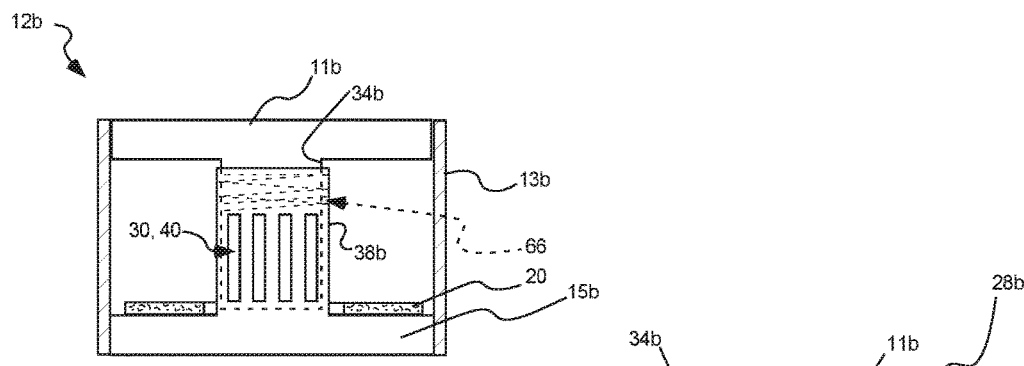
FIG. 4A is a side, partially sectioned view of a system for diffusing volatile compounds in accordance with another embodiment of the invention, shown in a sealed or closed configuration.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art having possession of this disclosure, are to be considered within the scope of the invention.

Definitions

As used herein, the singular forms "a" and "the" can include plural referents unless the context clearly dictates otherwise. Thus, for example, reference to "an airflow opening" can include one or more of such openings, if the context dictates. As used herein, the terms "downstream" and "upstream" are used to describe relative positions of various components as those components are encountered by a flow of a fluid. The terms "downstream" and "upstream" are relative to the fluid flow—they do not necessarily relate to a physical location of specific components. For example, a component that is generally perceived as being above or higher than another component can nevertheless be located downstream of that component, if the fluid flow so dictates.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms are sometimes used herein to describe and claim various components of the diffusion systems of the present invention. Such terms include, without limitation, "upward," "downward," "horizontal," "vertical," etc. These terms are generally not intended to be limiting, but are used to most clearly describe and claim the various features of the invention.

Where such terms must carry some limitation, they are intended to be limited to usage commonly known and understood by those of ordinary skill in the art having possession of this disclosure. For example, directional terms can be used herein to refer to various aspects of the present volatile compound diffusion systems in the case where the diffusion systems are used as a tabletop application. One of ordinary skill in the art will appreciate that the present systems can be used in a variety of other orientations, such as wall-mounted units or ceiling-mounted units. In these cases, the directional terms will, of course, apply differently to the system. One of ordinary skill in the art having possession of this disclosure will readily appreciate the adaptability of such terms to varying orientations of the present technology.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology provides systems and methods for controllably releasing various volatile compounds into an environment. Such volatile compounds include, without limitation, fragrant materials, pesticides, repellants, disinfectants, etc. In the interest of clarity, much of the discussion below will focus on the use of the technology to deliver fragrant material, as an air conditioner or freshener. It is to be understood, however, that the present invention is not limited to such applications and can be utilized in a variety of air treatment regimes in various environments.

On-demand or event-based fragrance delivery is a growing segment in the air care field. Consumers currently desire a product that can give quick, on-demand fragrancing in a product form that also offers the option to quickly change fragrance type, all while maintaining the convenience of a portable device. Currently, wax melt systems are often perceived as able to meet the need for on-demand fragrancing, but are limited to locations near an electrical outlet. Such wax-melt systems can also be overly messy, as once the wax is melted, it can splash easily. As such, changing fragrances quickly is not possible with these systems. Traditional, continuous action air fresheners take time to build up their fragrance level and are not designed to quickly change between fragrances.

The present technology provides a relatively simple device that utilizes very little power to quickly disperse fragrance into a room. A very efficient pod design is provided that allows pass-through airflow. As such, fan power can be utilized to deliver a very high amount of fragrance into the surrounding environment. Additionally, the pod can be resealed after and between uses to allow the user to exchange pods and fragrances very quickly.

As shown generally in FIGS. 1 and 2, in one aspect of the invention a system 10a is provided for diffusing one or more volatile compounds carried by a volatile compound mass 20. The system can include a base 16 carrying a selectively activatable airflow generator 22. The base can include a base outlet port 24 defined therein, with a pod platform 26 circumventing or otherwise defining the outlet port 24. As the airflow generator 22 generates airflow, the airflow is directed or focused by the platform through the outlet port and upward (in this embodiment) toward a resealable pod 12a. Air can be drawn into the base through base inlet ports 23.

Resealable pod 12a can include a tray 13, 15 and a cover 11. In the example shown, the tray includes at least one sidewall 13 that can be fixed to a bottom plate 15.

For purposes of the following discussion, reference to the tray includes both components 13, 15 shown. The tray and the cover 11 can be moveable relative to one another: in the embodiment shown in FIGS. 1-3C, the cover 11 moves vertically relative to the tray 13, 15, and vice versa. The tray and the cover can collectively define a containment chamber 28 that contains the volatile compound mass 20.

The containment chamber 28 can include a chamber inlet 30 (FIG. 2) and a chamber outlet 32. In the example shown in FIGS. 1 and 2, chamber inlet 30 includes a series of windows or openings 40 formed in a shaft 38 that extends at least partially through the tray 13, 15. The pod can include a rod 34 that extends downwardly from an upper plate 36 of the cover 11 and into shaft 38. In the position shown in FIG. 2, the pod is in an open configuration: rod 34 is extending into shaft 38 is but only partially lowered within the shaft. In this manner, windows 40 forming chamber inlet 30 are open to allow airflow from the base 15. In the example shown, chamber outlet 32 (FIG. 2) is formed when upper plate 36 is held above sealed engagement with the upper portion of sidewall 13.

When the cover 11 is fully lowered within the tray 13, 15, the shaft 34 blocks the interior portions of windows 40, which effectively seals chamber inlet 30. In addition, the upper plate 36 is lowered within the confines of outer wall 13, which results in chamber outlet 32 being sealed. Thus, the present technology provides a manner by which the chamber inlet 30 and outlet 32 can be openable and closeable by relative movement of the tray 13, 15 and the cover 11. In many embodiments, this can be accomplished simultaneously: the same relative movement that seals or opens the chamber inlet can also seal or open the chamber outlet.

As shown in FIG. 2, the pod 12a can be positioned upon the platform 26 of the base 16 such that the base outlet port 24 (FIG. 1) is in fluid communication with the chamber inlet 30. In this manner, airflow generated by the airflow generator 22 can pass through the base outlet port, through the chamber inlet, through the containment chamber 28, and through the chamber outlet 32. This airflow results in diffusion of the one or more volatile compounds carried by the volatile compound mass 20.

While the system 10a is shown in FIGS. 1 and 2 as including both a pod 12a and a base 16, in some embodiments, the system includes a stand-alone pod that can be delivered to consumers independently of a base. The consumer can use the pod as a stand-alone unit, if desired, or her or she can provide or obtain his or her own base that can provide airflow to the pod in accordance with the technology described herein.

Operation of the various components of the technology relative to one another can be further appreciated by the details provided in FIGS. 3A through 3C. In the configuration shown in FIG. 3A, the pod 12a is shown in a closed or sealed configuration. The windows 40 of chamber inlet 30 are blocked by the rod 34 extending downwardly from upper plate 36. Upper plate 36 forms a seal with outer wall 13, which effectively seals the chamber outlet (visible at 32 in FIG. 3C). In this view, it can be seen that rod 34 includes one or more sloped prongs 50 extending generally downwardly toward the upper plate or platform 26 of the base. The base 16 includes one or more sloped walls 52 that extend generally upwardly toward the pod upper plate 36 (in this example, the sloped walls are formed as an integral part of the platform 26 of the base 16). The tray 13, 15 can include one or more recesses 54 (two are shown in this view). Catches or protrusions 56 can be formed in each of the downwardly extending sloped prongs 50. In the configuration shown in FIG. 3A, each of two protrusions 56 is settled into recesses 54.

When in this position, the cover 11 is firmly held attached to the tray 13, 15, which in turn seals each of the chamber inlet 30 and chamber outlet 32. The pod 12a can be sold in this configuration, providing to the consumer a fresh volatile compound mass 20. As discussed in more detail below, the pod can be returned to this configuration after use, so that any unused volatile material can be used at a later date, without evaporating or otherwise dissipating during storage. This allows a consumer to quickly, and if desired, repeatedly change fragrance pods throughout the optimal life cycle of the pods without wasting volatile material between uses.

When a consumer wishes to use (or re-use) a pod, the pod can be positioned on the base 16 such that the sloped prongs 50 are aligned with the sloped walls 52, as shown in FIG. 3A. By applying downward pressure to the tray 13, 15, the sloped prongs are forced onto and around the sloped walls 52, as shown in FIG. 3B. Once enough pressure is applied, resulting in sufficient displacement of the sloped prongs relative to the sloped walls, the protrusion or catch 56 is forced sufficiently inwardly that it can clear the recess 54. At this point, the lid 11 can be freely slid upwardly relative to the tray 13, 15, which simultaneously results in the opening of chamber outlet 32 and chamber inlet 30. The pod can then be rested upon the pod platform 26. As airflow is generated by the airflow generator (22 in FIGS. 1 and 2), airflow can proceed downstream into the pod, through chamber inlet 40 (e.g., through windows 30), through the containment chamber 28, and out chamber outlet 32. As the airflow travels through the containment chamber, volatile compounds carried by the volatile compound mass are dispersed into the surrounding environment.

As also shown in FIG. 3C, in one example the resealable pod 12a can also include a pod inlet channel 58 that can be in fluid communication with chamber inlet 30. The inlet channel can extend from the base outlet port 24 upwardly into the tray 13, 15. A deflector panel 60 can be carried by the pod and can be positioned upstream of the chamber inlet 30. The deflector panel can be operable to direct airflow traveling through the pod inlet channel 58 into the chamber inlet 30 and thus into the containment chamber 28. In the example shown, the deflector panel substantially terminates the inlet channel 58 so that airflow can proceed no further along the channel. In one embodiment, the deflector plate is arranged substantially perpendicular to the airflow coming from the base. The present inventors have found that configuring the deflector panel in this manner causes significant disruption to the at least partially laminar flow emanating from the base. As a result, turbulence is caused in the airflow as the airflow transitions from the inlet channel 58 and into the containment chamber 28. As a result, the airflow to which the volatile compound mass is exposed causes a more effective release of the volatile compound from the mass 20.

Figure 4B:
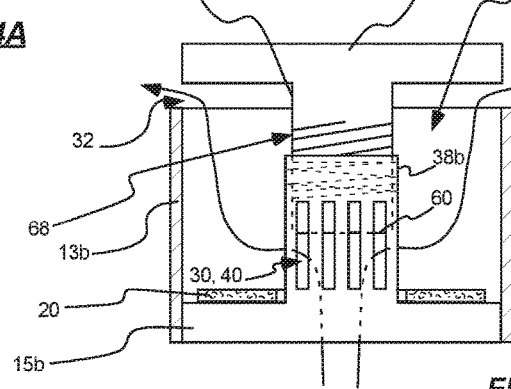
FIG. 4B is a side, partially sectioned view of the system of FIG. 4A, shown in an open configuration.

FIGS. 4A and 4B illustrate another embodiment of the invention in which pod 12b includes cover 11b and tray, which can be formed from outer wall 13b and base 15b. In this example, rod 34b is received by shaft 38b. Rod 34b can include external threads 68 (FIG. 4B) formed thereon, and shaft 38b can include internal threads 66 (FIG. 4A) formed therein. The shaft can include one or more windows or openings 40 formed therethrough. As shown in FIG. 4A, when the rod is fully received within the shaft, the rod serves to block the windows or openings, thereby closing the chamber inlet 30. By rotating the cover 11b relative to the tray 13b, 15b, the threaded connection between the two causes the cover 11b to be elevated relative to the tray 13b, 15b. As a result, chamber inlet 30 is opened, and chamber outlet 32 (FIG. 4B) is also opened (or created, as the case may be).

As in previous embodiments, the pod 12b can be delivered to consumers in the closed state shown in FIG. 4A, and can be easily returned to this state by a consumer after use. A consumer can easily use and reuse the pod while ensuring that it remains sealed between uses by simply rotating the cover 11b relative to the tray 13b, 15b to either open or close the pod. Also, as discussed in previous embodiments, the cover and tray can be moveable relative to one another in response to installation of the pod and tray upon a suitable base. That is, the cover and tray can be installed upon a base via a threaded connection. The same rotation that results in installing the pod upon a base can function to simultaneously open the pod.

Figure 5A:
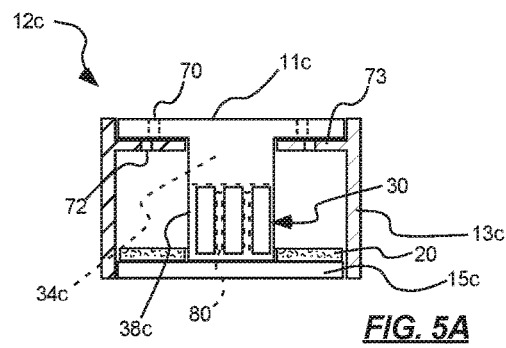
FIG. 5A is a side, partially sectioned view of a system for diffusing volatile compounds in accordance with another embodiment of the invention, shown in a sealed configuration.
Figure 5B:
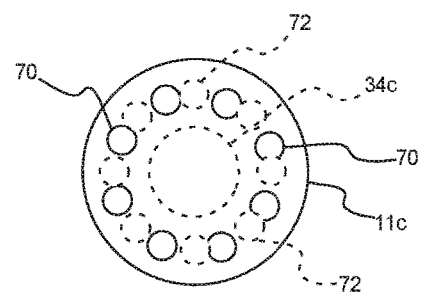
FIG. 5B is a top view of the system of FIG. 5A.
Figure 5C:
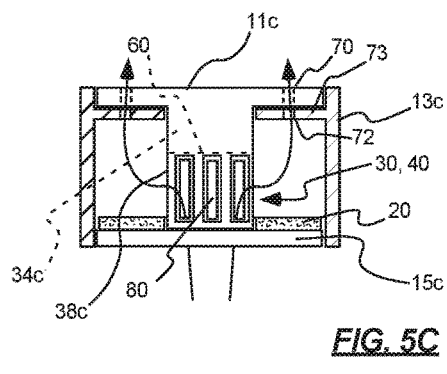
FIG. 5C is a side, partially sectioned view of the system of FIG. 5A, shown in an open configuration.
Figure 5D:
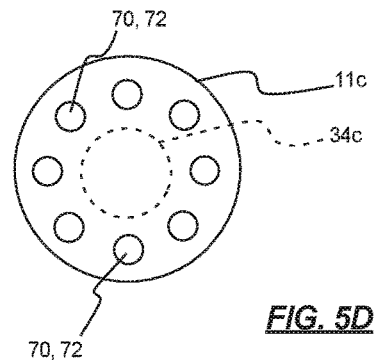
FIG. 5D is a top view of the system of FIG. 5C.

FIGS. 5A through 5D illustrate yet another embodiment of the invention. FIGS. 5A and 5B illustrate pod 12c in a closed or sealed configuration, and FIGS. 5C and 5D illustrate the pod in an open configuration. Pod 12c can include cover 11c and tray 13c, 15c. In this embodiment, the cover can include a series of openings 70 arranged across a top of the cover (see FIGS. 5B and 5D). Similarly, tray 13c, 15c can include an upper plate 73 having a series of openings 72 formed therein. As the cover 11c is rotated relative to the tray 13c, 15c, the openings 70 and 72 are aligned, thereby creating a chamber outlet.

The cover 11c can include a shaft 38c extending therefrom. Rod 34c can extend from tray 13c, 15c and can be received within the shaft. The shaft can include one or more windows or openings 40 formed therethrough. The rod can include one or more windows or openings 80 formed therein. By rotating the cover 11c and the tray 13c, 15c relative to one another, the windows 40 and 80 are aligned with another, thereby opening chamber inlet 30. This same rotation, as discussed above, causes the chamber outlet to also be opened.

As in previous embodiments, the pod 12c can be delivered to consumers in the closed state shown in FIGS. 5A and 5B, and can be easily returned to this state by a consumer after use. A consumer can easily use and reuse the pod while ensuring that it remains sealed between uses by simply rotating the cover 11c relative to the tray 13c, 15c to either open or close the pod. Also, as discussed in previous embodiments, the cover and tray can be moveable relative to one another in response to installation of the pod and tray upon a suitable base. That is, the cover and tray can be openable as the pod is placed upon or installed with a base.

The volatile compound mass 20 can be formed from a variety of materials. Suitable compositions include, without limitation, scented aqueous gels, scented non-aqueous gels, waxes, permeable membranes, or fragrance-infused absorbent material such as paper, fibrous masses, ceramic, porous plastic, wood, or inorganic porous solids (i.e. salt), etc. Generally, exposure of the volatile compound mass to the environment results in one or more volatile compounds being released into the environment to act as a fragrant agent, insecticide, pesticide, disinfectant, etc. In the examples shown in the present disclosure, the mass 20 is at least partially solid, so that it retains its shape independently of any structure housing the mass.

The volatile compound mass 20 is shown by example in the figures as having a generally toroidal shape, with a relatively low height extending upwardly into the containment chamber 28. In the examples shown, airflow traveling through windows 40, for example, will generally travel over an upper surface of the volatile compound mass. In some embodiments, however, the mass 20 can be formed in differing sizes and shapes than those shown. For example the mass 20 can include a greater height than that shown, and can be spaced slightly from the rod 34 and/or shaft 38. In this manner, airflow traveling from windows 40 will encounter one or more inner sides of the mass, will travel upwardly relative to this side, and around and/or over an upper surface of the mass.

The airflow generator 22 can take a variety of forms, and can be controlled and powered in a variety of manners. The various components required to power and/or operate the airflow generator are not shown in detail. However, one of ordinary skill in the art having possession of this disclosure can readily understand the various power sources, circuitry, switches, etc., that can be incorporated into the present technology to generate airflow in the base 16.

The airflow generator 22 can be powered by simple household AC current, or a DC battery source. Solar power can utilized by incorporation a number of suitable components, as can low-voltage power sources such as USB power connections, etc.

A mechanical power source can also be utilized, for example, with a "wind-up" mechanism that stores energy in the form of springs and/or similar components. Such mechanisms are known for use in analogous applications, such as timepieces, animatronics, toys, etc. As the airflow generator can have very low power demand, a variety of portable power supplies can be used to provide sufficient power while enabling portability.

In addition to the structural components discussed above, the present invention also provides various methods of diffusing volatile compounds carried by a pod, methods of installing diffusion pods within an activation system, methods of treating or conditioning an environment with volatile compounds, and methods of closing or sealing, and conversely opening, volatile compound pods.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. A system for diffusing one or more volatile compounds carried by a volatile compound mass, the system comprising:
   a base carrying a selectively activatable airflow generator and having a base outlet port defined therein;
   a resealable pod, including:
      a tray and a cover, moveable relative to one another, the tray and the cover collectively defining a containment chamber that contains the volatile compound mass, the containment chamber having an inlet and an outlet, the chamber inlet and outlet being openable and closeable by relative movement of the tray and the cover;
   the pod being positionable upon the base such that the base outlet port is in fluid communication with the chamber inlet to enable airflow generated by the airflow generator to pass through the base outlet port, through the chamber inlet, through the containment chamber, and through the chamber outlet to thereby diffuse the one or more volatile compounds carried by the volatile compound mass.

2. The system of claim 1, wherein the resealable pod further includes a pod inlet channel, in fluid communication with the chamber inlet; and further comprising:
   a deflector panel, carried by the pod and being positioned upstream of the chamber inlet, the deflector panel operable to direct airflow traveling through the pod inlet channel through the chamber inlet and into the containment chamber.

3. The system of claim 1, wherein the base includes a pod platform operable to receive the pod thereupon, the pod platform circumscribing the base outlet port to thereby direct flow from the base through the base outlet port.

4. The system of claim 1, wherein one of the tray and the cover includes a shaft extending at least partially therethrough, the shaft defining a pod inlet channel, the shaft including one or more windows formed therethrough.

5. The system of claim 4, wherein an other of the tray and the cover includes a rod, extending into the shaft, the rod including a deflector panel that directs airflow from the pod inlet channel through the windows and into the containment chamber.

6. The system of claim 5, wherein the rod is positionable behind the windows to thereby block airflow through the windows.

7. The system of claim 1, wherein the cover includes an upper plate, and wherein the tray includes at least one side wall, and wherein the chamber outlet is created when the upper plate moves relative to the at least one side wall.

8. The system of claim 1, further comprising:
   pod engagement structure coupled to the base; and
   base engagement structure, coupled to the pod, the base engagement structure operable to move the tray and cover relative to one another when the pod engagement structure is engaged by the base engagement structure;
   the pod being positionable upon the base such that when the base outlet port is placed in fluid communication with the chamber inlet, the base engagement structure engages the pod engagement structure to move the tray and cover relative to one another to cause the chamber inlet and outlet to open.

9. A system for diffusing one or more volatile compounds carried by a volatile compound mass, the system comprising:
   a resealable pod, including:
      a tray and a cover, moveable relative to one another, the tray and the cover collectively defining a containment chamber that contains the volatile compound mass, the containment chamber having an inlet and an outlet, the chamber inlet and outlet being openable and closeable by relative movement of the tray and the cover;
   the pod being positionable upon a base carrying a selectively activatable airflow generator such that an outlet port of the base is in fluid communication with the chamber inlet to enable airflow generated by the airflow generator of the base to pass through the base outlet port, through the chamber inlet, through the containment chamber, and through the chamber outlet to thereby diffuse the one or more volatile compounds carried by the volatile compound mass.

10. The system of claim 9, further comprising a base carrying a selectively activatable airflow generator and having a base outlet port formed therein.

11. The system of claim 10, further comprising a pod inlet channel, in fluid communication with the chamber inlet; and
   a deflector panel, positioned upstream of the chamber inlet, the deflector panel operable to change a direction of airflow traveling through the pod inlet channel;
   the pod being positionable upon the base such that the base outlet port is in fluid communication with the pod inlet channel to enable airflow generated by the airflow generator to pass through the base outlet port, through the pod inlet channel, through the chamber inlet, through the containment chamber, and through the chamber outlet to thereby diffuse the one or more volatile compounds carried by the volatile compound mass.

12. The system of claim 10, wherein the base includes a pod platform operable to receive the pod thereupon, the pod platform circumscribing the base outlet port to thereby direct flow from the base through the base outlet port.

13. The system of claim 10, wherein one of the tray and the cover includes a shaft extending at least partially therethrough, the shaft defining a pod inlet channel, the shaft including one or more windows formed therethrough.

14. The system of claim 13, wherein an other of the tray and the cover includes a rod, extending into the shaft, the rod including a deflector panel that directs airflow from the pod inlet channel through the windows and into the containment chamber.

15. The system of claim 14, wherein the rod is positionable behind the windows to thereby block airflow through the windows.

16. A system for diffusing one or more volatile compounds carried by a volatile compound mass, the system comprising:
   a base carrying a selectively activatable airflow generator and having a base outlet port defined therein;
   pod engagement structure coupled to the base;

a resealable pod, including:
- a tray and a cover, moveable relative to one another, the tray and the cover collectively defining a containment chamber that contains the volatile compound mass, the containment chamber having an inlet and an outlet, the chamber inlet and outlet being openable and closeable by relative movement of the tray and the cover; and
- base engagement structure, coupled to the pod, the base engagement structure operable to move the tray and cover relative to one another when the pod engagement structure is engaged by the base engagement structure;
- the pod being positionable upon the base such that when the base outlet port is placed in fluid communication with the chamber inlet, the base engagement structure engages the pod engagement structure to move the tray and cover relative to one another to cause the chamber inlet and outlet to open.

17. The system of claim 16, wherein the base engagement structure extends from the cover of the pod, and wherein the pod engagement structure extends from the base and through the tray of the pod.

18. The system of claim 17, wherein the base engagement structure includes one or more sloped prongs extending from the cover, and further comprising one or more notches formed in the tray, the sloped prongs being receivable within the notches to fix a position of the cover relative to the tray.

19. The system of claim 17, wherein the pod engagement structure includes one or more sloped walls extending from the base, and wherein movement of ends of the sloped prongs along the sloped walls causes the prongs to be displaceable from the notches to allow the tray to move relative to the cover.

20. The system of claim 16, wherein the pod further includes a pod inlet channel, in fluid communication with the chamber inlet; and further comprising:
- a deflector panel, carried by the pod and being positioned upstream of the chamber inlet, the deflector panel operable to direct airflow traveling through the pod inlet channel through the chamber inlet and into the containment chamber.

\* \* \* \* \*